United States Patent
Lord et al.

(10) Patent No.: US 8,425,493 B2
(45) Date of Patent: Apr. 23, 2013

(54) IMPLANTABLE MEDICATION DELIVERY DEVICE

(75) Inventors: Peter C. Lord, Valencia, CA (US);
Clyde K. Nason, Wasco, CA (US);
Darren Y. K. Yap, Valencia, CA (US);
Stephen D. Das, The Woodlands, TX (US); Ronald J. Lebel, Sherman Oaks, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 1979 days.

(21) Appl. No.: 10/515,152

(22) PCT Filed: May 20, 2003

(86) PCT No.: PCT/US03/16329
§ 371 (c)(1),
(2), (4) Date: Dec. 19, 2005

(87) PCT Pub. No.: WO03/099351
PCT Pub. Date: Dec. 4, 2003

(65) Prior Publication Data
US 2006/0122578 A1 Jun. 8, 2006

Related U.S. Application Data

(60) Provisional application No. 60/383,237, filed on May 22, 2002.

(51) Int. Cl.
*A61K 9/22* (2006.01)
(52) U.S. Cl.
USPC ............ 604/891.1; 604/288.01; 604/288.02; 604/288.04; 604/288.03; 604/890.1; 604/131; 604/141; 604/67; 604/152; 604/153

(58) Field of Classification Search ............... 604/890.1, 604/891.1, 67, 141, 153, 288.02, 288.04, 604/131, 288.01, 288.03
See application file for complete search history.

(56) References Cited

U.S. PATENT DOCUMENTS

| | | | |
|---|---|---|---|
| 4,265,600 A | 5/1981 | Mandroian | |
| 4,265,601 A | 5/1981 | Mandroian | |

(Continued)

FOREIGN PATENT DOCUMENTS

| | | |
|---|---|---|
| WO | WO 99/38551 A1 | 8/1999 |
| WO | WO 01/58506 A2 | 8/2001 |

OTHER PUBLICATIONS

D Accoto, et al., Modelling of micropumps using unimorph piezo-electric actuator and ball valves, J. Micromech. Microeng, 10 (2000) 277-281, IOP Publishing Ltd, UK.

(Continued)

*Primary Examiner* — Kevin C Sirmons
*Assistant Examiner* — Edelmira Bosques
(74) *Attorney, Agent, or Firm* — Henricks, Slavin & Holmes LLP (57) ABSTRACT

An implantable medication delivery device that is highly space efficient and can reliably and safely deliver controlled medication doses to a target site. The system includes a variable volume medication reservoir that is exposed to an ambient pressure equal to the ambient pressure at a system outlet port. A pump/valve subassembly is provided to draw medication from the reservoir and force a medication dose along a fluid transfer passageway to the outlet port. The pump/valve subassembly incorporates a safety mechanism, e.g., a balanced valve, which normally blocks medication flow to the outlet port and opens only in response to a pump induced unbalancing force. A protective shell is also disclosed for protecting the ambient reservoir.

12 Claims, 6 Drawing Sheets

U.S. PATENT DOCUMENTS

| | | | |
|---|---|---|---|
| 4,548,607 A * | 10/1985 | Harris | 604/891.1 |
| 4,594,058 A | 6/1986 | Fischell | |
| 4,668,231 A * | 5/1987 | de Vries et al. | 604/891.1 |
| 5,704,520 A | 1/1998 | Gross | |
| 5,954,058 A | 9/1999 | Flaherty | |
| 5,957,890 A | 9/1999 | Mann et al. | |
| 6,280,416 B1 | 8/2001 | Van Antwerp et al. | |
| 6,656,158 B2 | 12/2003 | Mahoney et al. | |

OTHER PUBLICATIONS

Supp. Search Report Dated Jul. 23, 2008 in EPO App. Ser. No. 03 755 456.5.

* cited by examiner

IMPLANTABLE MEDICATION DELIVERY DEVICE

RELATED APPLICATIONS

This application claims the benefit of U.S. Application 60/383,237 filed on 22 May 2002.

FIELD OF THE INVENTION

The present invention is directed to implantable medication delivery devices useful for delivering prescribed medication doses to targeted body sites.

BACKGROUND OF THE INVENTION

Commercially available implantable medication delivery devices are exemplified by a Synchromed product marketed by Medtronic (of Minneapolis, Minn., USA) and a MIP product manufactured by Minimed, now a division of Medtronic. Both of these devices employ a medication reservoir comprising a bellows that contracts as medication is extracted by a pump mechanism. The reservoir volume change is accommodated by a second chamber which contains a propellant such as Freon in a gas/liquid equilibrium. The propellant functions to maintain a constant absolute pressure at body temperature. In the case of the MIP product, the propellant is a liquid at body temperature creating a negative pressure reservoir. In the case of the Syncromed product, the propellant is a gas at body temperature creating a positive pressure reservoir. In both cases, the medication reservoir is maintained at a constant absolute pressure by the propellant. Although the reservoir, and therefore the inlet side of the pump mechanism are at a constant absolute pressure, the tip of an output catheter and thus the outlet of the pump mechanism, are at ambient pressure. Ambient pressure typically varies as a function of environmental conditions including local barometric pressure and altitude, etc. In addition, variations in temperature can produce variations in reservoir pressure. The combined effect of these conditions can produce pressure differences in excess of 500 millibars across the pump mechanism. In order to seal and pump across a pressure difference of this magnitude, these exemplary systems require pumps of a size which are not well suited for implantation in space limited sites, e.g., the brain, eye, or ear.

SUMMARY OF THE INVENTION

The present invention is directed to a medication delivery device comprising an ambient reservoir and housing integrated so as to be highly space efficient for reliably and safely delivering controlled medication doses to a target body site. Devices in accordance with the invention include a mounting structure for supporting a reservoir peripheral wall which includes a movable, e.g., flexible, portion. The reservoir wall has an outer surface exposed to an ambient pressure (equal to the pressure at the tip of an output catheter) which establishes the same pressure within the reservoir interior volume. As a consequence of the reservoir and catheter tip being at the same pressure, the pump size and energy requirements are reduced as compared to the aforementioned exemplary prior art systems.

In accordance with the invention, the reservoir wall encloses a variable volume for storing medication. The movable reservoir wall portion can be formed of flaccid nonextensible nonporous material or, alternatively, can be formed by a bellows or telescoping tubular sections. The mounting structure for supporting the reservoir wall preferably incorporates a pump/valve subassembly operable to draw medication from the reservoir via a fluid inlet and force medication along a fluid transfer passageway to an outlet port adapted to be coupled to the output catheter.

In order to reliably use an ambient pressure reservoir, a device in accordance with the invention is configured to prevent medication leakage (or flowthrough), i.e., unintended medication discharge through the outlet port, as a result of reservoir overfill and/or a pressure or force being applied to the reservoir. More particularly, it is unacceptable for medication to be discharged as a result of the reservoir wall being pressed, e.g., as a consequence of the patient being bumped. Thus, in accordance with a first preferred embodiment, the aforementioned pump/valve subassembly incorporates a safety mechanism which functions to normally block unintended fluid flow to the outlet port. One preferred safety mechanism in accordance with the invention uses a balanced valve which responds to a difference between the reservoir pressure and a pump chamber pressure. That is, an increase in reservoir pressure acts in a direction to seal closed the safety mechanism valve whereas an increase in pump chamber pressure acts to open the valve to effectively disable its normal blocking function.

In accordance with an alternative and/or additional feature for preventing medication flowthrough, a protective substantially rigid shell is mounted around the reservoir wall to prevent the inadvertent application of a force thereto. In order to maintain ambient pressure in the reservoir, the shell is configured to allow body fluid to enter and exit the shell to enable the reservoir to expand (when being filled with medication) and contract (as medication is being discharged). In accordance with a second preferred embodiment, the shell includes a diffusive membrane (e.g., cellulose acetate membrane) that permits body fluid to flow slowly into the shell interior volume but prevents undesirable tissue growth therein. The shell preferably also includes a check valve which permits relatively rapid fluid outflow to permit the reservoir to fill and expand within the shell interior volume.

A preferred mounting structure in accordance with the invention supports the reservoir wall and functionally integrates the pump/valve subassembly. The pump/valve subassembly includes an inlet port and a fluid passageway extending to an outlet port. A first check valve, permitting fluid inflow only is included in the passageway downstream from the fluid inlet. A pump chamber is included in the passageway between the first check valve and a safety mechanism located upstream from the outlet port. A pump element coupled to the pump chamber is operable to produce (1) a suction for drawing medication past the first check valve into the pump chamber and (2) a pressure for expelling medication from the pump chamber toward said safety mechanism.

As previously mentioned, the safety mechanism is provided to prevent unintended medication flow to the outlet port. The safety mechanism includes a valve element movable between (1) a flow position and (2) a flow-block position. In a preferred embodiment, the safety valve element is normally in the flow-block position. However, a pressure increase in the pump chamber produced by the pump element acts to move the safety valve element to the flow position thus temporarily disabling the flow blocking function.

DETAILED DESCRIPTION

Figure 1:
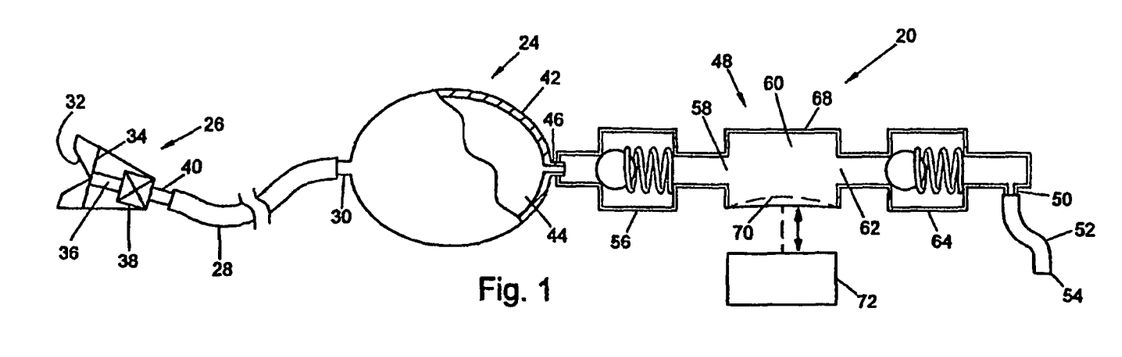
FIG. 1 is a schematic block diagram of a basic ambient pressure medication delivery system.

Attention is initially directed to FIG. 1 which schematically depicts an implantable medication delivery system 20 including a variable volume reservoir 24 for storing medication. The reservoir 24 is preferably refillable, e.g., via a fill device 26 and tube 28 coupled to a reservoir fill port 30. The fill device 26 preferably defines a conical entrance 32 for guiding the needle of a syringe (not shown) through a self healing septum 34 to a channel 36 and check valve 38. The outlet of check valve 38 is coupled via nipple 40 to the upstream end of tube 28. The downstream end of tube 28 is coupled to the reservoir fill port 30.

The variable volume reservoir 24 is comprised of a wall 42 including at least a portion supported for movement to enable the reservoir interior volume 44 to expand and contract. Although the reservoir 24 is most simply formed of flexible, or flaccid, nonextensible nonporous material forming a sack, it can also be provided in various alternative configurations. For example, the reservoir 24 can be configured as a bellows, telescoping tubular sections, or as a shaped rubber boot having a stiffened base such that the base lifts and the boot's sidewall rolls upon itself, as the reservoir interior volume changes.

The reservoir outlet 46 is coupled via a fluid passageway 48 to a system output port 50. The system output port 50 is typically coupled to a catheter 52 whose downstream end, or tip 54, is intended to infuse medication into targeted body tissue, e.g., brain tissue, blood or intraperitoneal space. The fluid passageway 48 is comprised of a first, or upstream, check valve 56 which leads to an entrance port 58 of a pump chamber 60. A pump chamber exit port 62 is coupled to a second, or downstream, check valve 64 which leads to the aforementioned system output port 50.

The pump chamber 60 is defined by a peripheral wall 68 including a movable portion, e.g., a piston or diaphragm 70. The diaphragm 70 is coupled to an actuator 72 configured to displace the diaphragm 70 reciprocally between a first position which contracts the volume of the pump chamber 60 and a second position which expands the volume of the chamber 60. Thus, when the diaphragm 70 moves downwardly as represented in FIG. 1, the pump chamber 60 will expand in volume creating a negative pressure which draws medication from the interior reservoir volume 44 past the check valve 56 into the pump chamber 60. On the other hand, when the diaphragm 70 moves upwardly, as represented in FIG. 1, a portion, or dose, of the medication in chamber 60 will be expelled through exit port 62 past check valve 64 to the system output port 50.

Figure 3:
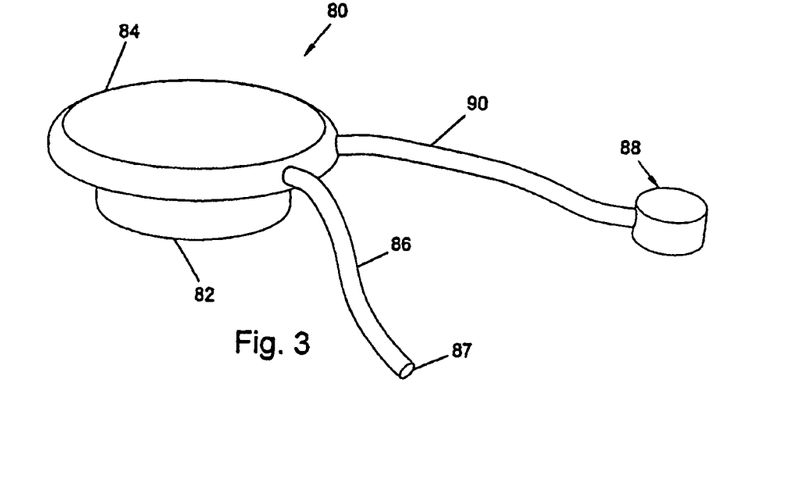
FIG. 3 is an isometric exterior view of a preferred implantable medication delivery system in accordance with the present invention.

A system of the type represented in FIG. 1 is intended in accordance with the invention to be implanted in a patient's body such that the reservoir wall 42 and the catheter tip 54 are both exposed to substantially the same ambient pressure. An isometric exterior view of an exemplary embodiment 80 in accordance with the invention is shown in FIG. 3. Note that the embodiment 80 includes a housing 82 carrying an integrated reservoir 84, analogous to the aforedisccussed reservoir 24, of FIG. 1. Also note that a catheter tube 86, analogous to the aforementioned catheter tube 52, extends outwardly from the housing 82. Further note that a fill device 88, analogous to aforedisccussed fill device 26, is coupled to the housing 82 via a fill tube 90.

Figure 4:
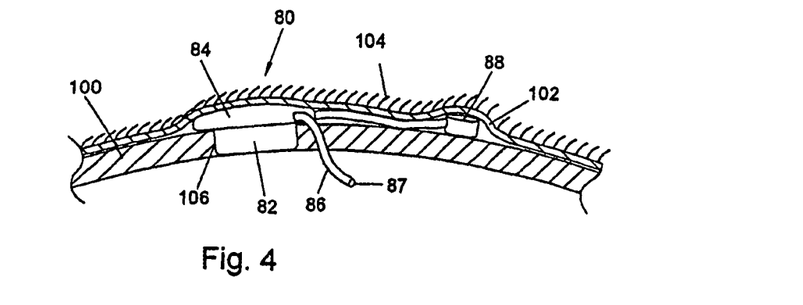
FIG. 4 is a cross-sectional view showing the system of FIG. 3 implanted at an exemplary site in a patient's body for infusing medication into the patient's brain.

FIG. 4 depicts an exemplary embodiment 80 implanted in a patient's body in accordance with one significant application of the invention as a cranial pump for delivering medication to brain tissue. Embodiments of the invention can be advantageously used in a variety of other applications, e.g., eye, ear, brain. Note that FIG. 4 represents a patient's skull at 100 covered by a patient's skin 102 and hair 104. In the contemplated implant procedure for the embodiment 80, a recess 106 is surgically formed in the patient's skull for accommodating the housing 82. The reservoir portion 84 of the embodiment 80 lies beneath the skin 102 as depicted. The fill device 88 is also shown as being subcutaneously implanted. As is well known, the subcutaneous fill device 88 can be used together with a syringe to fill reservoir 84 with fluid medication. FIG. 4 also depicts the output catheter 86 extending from the device 80 with the catheter tip 87 positioned to infuse medication into the patient's brain.

In order to use an ambient pressure reservoir in the medication delivery system exemplified by FIG. 1 and implanted in the exemplary manner shown in FIG. 4, various problems have to be addressed to insure patient safety and device reliability. One such problem is to prevent medication discharge from catheter tip 87 as a consequence of inadvertently overfilling the reservoir and/or unintentionally applying a force to the reservoir wall 42. That is, it is important in accordance with the invention to prevent flowthrough, i.e., an unintended delivery of medication as a consequence, for example, of a physician over pressurizing the reservoir by introducing too much medication and/or the patient being bumped or pressing the reservoir wall.

Figure 2:
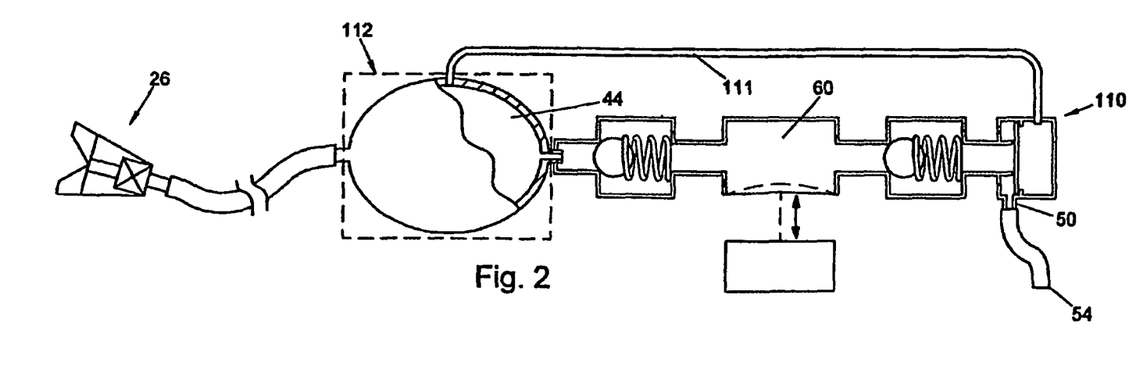
FIG. 2 is a schematic block diagram similar to FIG. 1 modified to represent two alternative features for preventing medication discharge as a consequence of a force applied to the medication reservoir, namely (1) a safety mechanism responsive to an applied force for blocking flow to the output port and (2) a protective shell mounted around the reservoir.

Thus, preferred embodiments of the invention, as detailed in FIGS. 5-11, incorporate (1) a safety mechanism for preventing medication flowthrough in the event of a pressure increase in the reservoir, e.g., attributable to a force exerted against the reservoir wall and/or (2) a protective shell around the reservoir to prevent the inadvertent application of a force to the reservoir wall. FIG. 2 depicts a modification of the ambient pressure reservoir medication delivery system of FIG. 1 to show the inclusion of an exemplary (1) safety mechanism 110 responsive to reservoir pressure via channel 111 and (2) protective reservoir shell 112. The safety mechanism 110 and protective shell 112 can be used separately or in combination.

Figure 5:
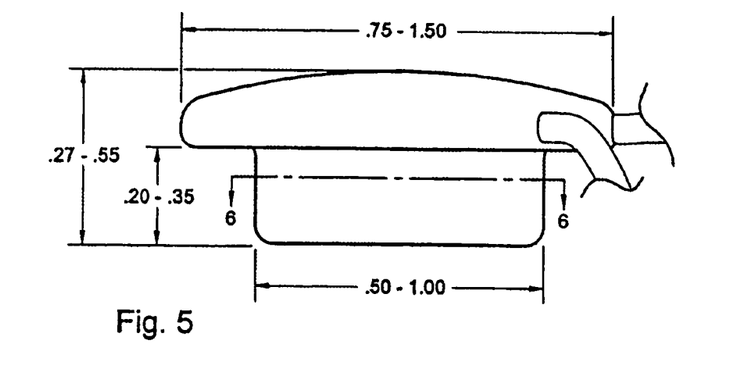
FIG. 5 is an exterior side view of a preferred embodiment showing exemplary dimensions.
Figure 6:
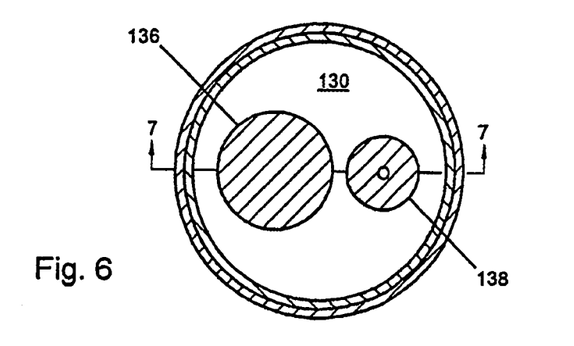
FIG. 6 is a horizontal sectional view taken substantially along the plane 6-6 of FIG. 5.

Attention is now directed to FIGS. 5-8 which show the details of a first embodiment of the invention, consistent with the exterior representation shown in FIGS. 3 and 4, and incorporating the safety mechanism 110 of FIG. 2. FIG. 5 comprises an exterior side view of the embodiment depicted in FIG. 3 showing exemplary dimensions (inches) for presently contemplated implant applications. The following table shows exemplary specifications for the applications indicated:

| Parameter | Very Small Pump; Very Low Delivery Rate | | | Small Pump; Low Delivery Rate | | |
|---|---|---|---|---|---|---|
| | Typical | Min | Max | Typical | Min | Max |
| Medication Reservoir Volume (ml) | 3 | 0.5 | 5 | 20 | 5 | 40 |
| Daily Delivery Rate (ml/day) | 0.05 | 0.03 | 0.1 | 0.33 | 0.1 | 0.66 |
| Maximum Delivery Rate (ul/minute) | 3 | 1 | 10 | 30 | 5 | 120 |
| Stroke Volume (microliters) | 0.2 | 0.05 | 1 | 0.5 | 0.1 | 5 |
| Maximum Output Pressure (psig) | 14.7 | 7 | 100 | 14.7 | 7 | 100 |
| Longevity (years) | 8 | 3 | 10 | 8 | 3 | 10 |
| Refill Interval (days) | 60 | 30 | 90 | 60 | 30 | 90 |
| Application (typical) | Tinnitus using lidocaine | | | Pain using morphine; Spasticity (CP) using baclofen | | |
| Route of Delivery | Intracranial, eye, ear | | | Intrathecal, epidural, Intraperitoneal, systemic | | |

The medication delivery device depicted in FIGS. 5-8 is comprised of a housing 120 formed by a bowl-shaped wall 122 that includes a horizontally oriented (as viewed in FIG. 7) circular base 124 having a cylindrical side wall 126 extending vertically therefrom. The upper edge of sidewall 126 flairs radially outward to form a horizontal flange 128. A circular partition plate 130 is supported above the base 124 to form a closed compartment for housing a battery 132 (preferably remotely chargeable). The upper surface of partition plate 130 is preferably used to support an electronic control module 136 and an electrically driven pump actuator 138, analogous to the aforementioned actuator 72. A substantially planar pump/valve subassembly 140 is supported on the upper surface of flange 128 above the module 136 and pump actuator 138.

Figure 7:
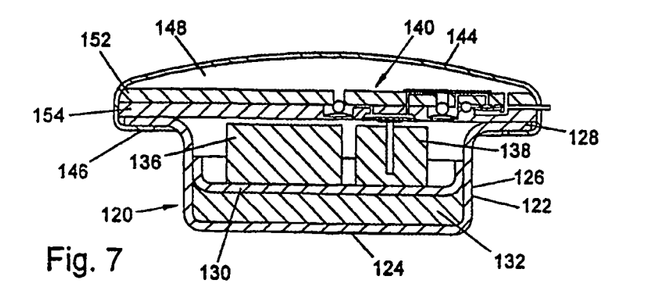
FIG. 7 is a vertical sectional view taken substantially along the plane 7-7 of FIG. 6.

The housing 120 and subassembly 140 together form a mounting structure for supporting a reservoir wall 144 of nonextensible nonporous material which extends loosely over the subassembly 140. The peripheral edge 146 of wall 144 is preferably sealed to the under surface of flange 128 to thus form a closed reservoir volume 148 above the upper surface of subassembly 140 for storing fluid medication.

Figure 8:
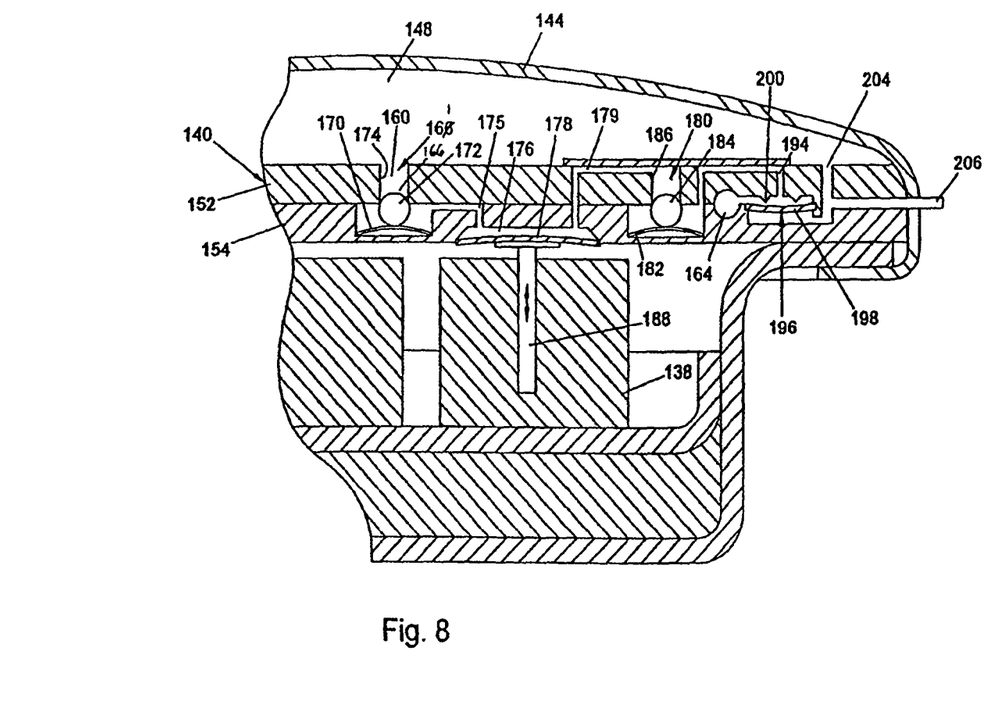
FIG. 8 is an enlarged sectional view showing a preferred pump/valve assembly in accordance with a first embodiment of the invention.

The pump/valve subassembly 140 preferably comprises a thin flat structure formed by laminating two or more plates 152, 154. The laminated plates can be formed and assembled using a variety of materials, e.g., titanium, stainless steel, silicon, plastic, etc. and known fabrication techniques appropriate to the materials and the desired dimensions and tolerances.

With continuing reference to FIG. 8, note that upper plate 152 defines an inlet port 160 of a fluid passageway 161 leading to an outlet port 164. The fluid passageway 161 includes a first check valve 166, located just downstream form inlet port 160. Check valve 166 is preferably comprised of spring 170 that normally seals a precision ball 172 against valve seat 174. The outlet of check valve 166 opens via port 175 to pump chamber 176 whose peripheral wall is defined in part by flexible diaphragm 178. The pump chamber outlet 179 leads to the inlet of a second check valve 180 preferably comprised of spring 182 normally sealing ball 184 against valve seat 186.

The pump diaphragm 178 is mounted for movement, as by coupling it to a stem 188 of the linear actuator 138. When the actuator 138 pulls the stem downward (as viewed in FIG. 8) to increase the volume of pump chamber 176, the resulting suction draws medication past check valve 166 into the pump chamber 176. When the actuator 138 drives the stem 188 upward, the diaphragm 178 produces a positive pressure to expel medication from the pump chamber 176 past the second check valve 180 toward the outlet port 164. For simplicity of explanation herein, the actuator has been described as pulling the stem downward and driving the stem upward. It should be understood however, that the diaphragm could, in fact, be biased to one position so that the actuator need only move it from the biased position The outlet of check valve 180 opens via port 194 to safety valve 196, analogous to safety mechanism 110 of FIG. 2. Safety valve 196 is preferably comprised of a flexible, e.g., elastomeric, valve disc 198 mounted so that its upper surface normally seals against the valve seat 200 (flow-block position) in the absence of a force produced by an upward stroke of diaphragm 178. More particularly, When the actuator 138 is dormant, the upper face of valve disc 198 is exposed to ambient reservoir pressure via check valves 166 and 168. The lower face of valve disc 198 is also exposed to ambient reservoir pressure via channel 204, analogous to channel 111 of FIG. 2. Parenthetically, note also that channel 204 defines a path from fill nipple 206, analogous to input 30 of FIG. 1, to the reservoir volume interior 148.

Under normal conditions with the actuator 138 dormant, ambient reservoir pressure is applied to both faces of valve disc 198 and it remains in a flow-block position sealed against valve seat 200 so as to block outflow from check valve 180 to output port 164. If the reservoir pressure increases, e.g., attributable to the patient being bumped or pressing the reservoir wall, the pressure will increase equally on both faces of the valve disc 198, thereby leaving the disc 198 seated. Thus, the inclusion of safety valve 196 upstream from outlet port 164 prevents a failure mode which could, in the absence of the safety valve, unintentionally force medication out through the outlet port 164. When the actuator 138 is activated, however, the upward movement of diaphragm 178 forces medication from the pump chamber 176 past the check valve 180 to the upper face of valve disc 198. The resulting unbalanced pressure on valve disc 198 unseats the disc thereby disabling its flow blocking function to permit medication to flow therepast to the outlet port 164.

Figure 9:
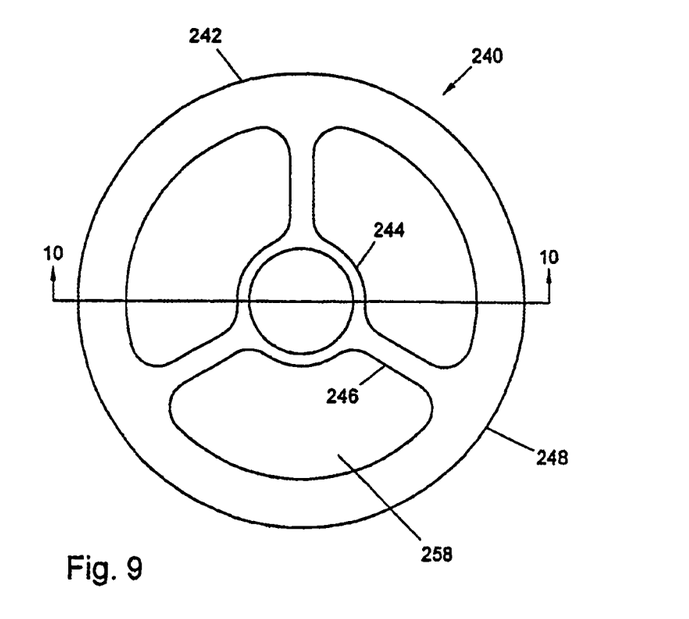
FIG. 9 is a plan view of a second embodiment of the invention incorporating a protective shell around the reservoir.
Figure 10:
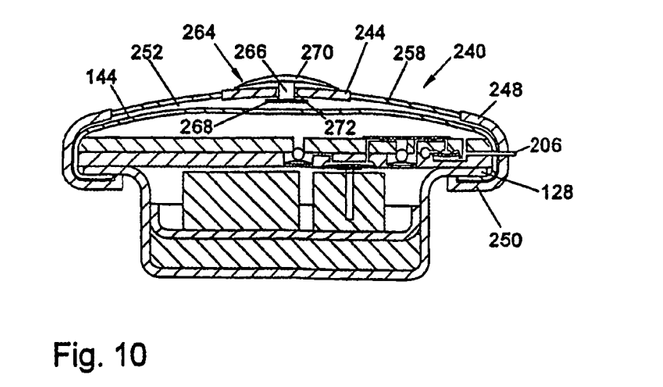
FIG. 10 is a sectional view taken substantially along the plane 10-10 of FIG. 9.

Attention is now directed to FIGS. 9 and 10 which illustrate a preferred protective shell 240 (corresponding to shell 112 of FIG. 2) configured to protect the reservoir wall 144 from impact, while still exposing it to ambient pressure and allowing it to expand and contract. The shell 240 preferably comprises a dome-shaped rigid or semi-rigid frame 242 including a hub 244 and radial arms 246 extending to an outer ring 248. The outer ring 248 carries inwardly extending flange portions 250 configured to mount around housing flange 128. The shell 240 is shaped and dimensioned to define an interior volume 252 able to snugly accommodate reservoir wall 144 in its fully expanded state.

In order to expose the reservoir wall 144 to ambient pressure and permit it to expand and contract within the shell interior volume 252, means are provided to allow body fluid to enter into and exit from the interior volume 252. More particularly, a diffusive membrane 258 preferably formed of a cellulose acetate or similar material, is mounted between the hub 244 and outer ring 248. The diffusive membrane material is preferably selected to permit slow diffusion of body fluids into the volume 252 while preventing the in-growth of body tissue. A slow rate of fluid inflow is acceptable because, in typical applications, the reservoir will contract at a maximum rate of only about 40 milliliters per month.

On the other hand, when the reservoir is refilled via fill nipple 206, a greater rate of outflow from the volume 252 is required. Accordingly, an outflow check valve 264 is preferably mounted in the hub 244 to allow the reservoir to expand relatively rapidly and force fluid out of the volume 252. Check valve 264 is comprised of a stem 266 carrying a retention rod 268 on its lower end and a sealing disc 270 on its upper end. When the reservoir expands, it increases the pressure in volume 252 to lift disk 270 permitting the outflow of fluid through opening 272 around stem 266.

Figure 11:
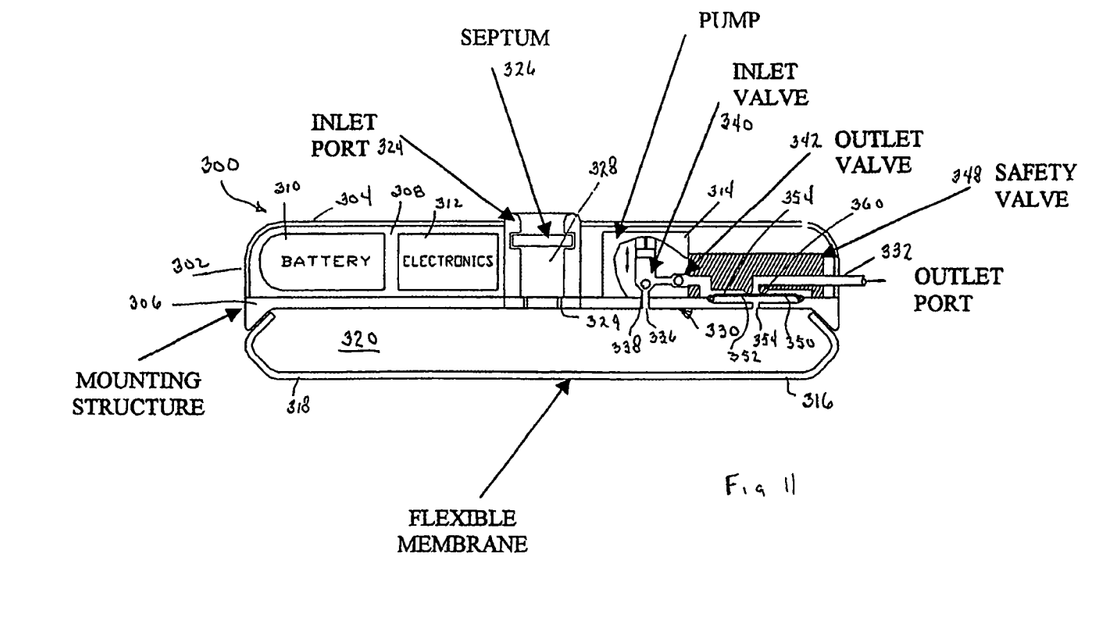
FIG. 11 is a sectional view of an alternative preferred embodiment of this invention.

Attention is now directed to FIG. 11 which schematically illustrates an alternative preferred medication delivery device 300 in accordance with the present invention. The device 300 is comprised of a housing 302 including a top cover plate 304 and a bottom plate 306. The spaced plates 304, 306 define an interior compartment 308 for housing a battery 310, electronics 312, and a pump 314. The housing 302 and plate 306 form a mounting structure for supporting a flexible membrane 316. The membrane 316 preferably comprises flaccid nonextensible nonporous material which acts as a peripheral wall 318 enclosing an interior reservoir volume 320.

The spaced plates 304, 306 support a reservoir fill port 324 which includes a self healing septum 326. The reservoir volume 320 can be filled by a hypodermic needle (not shown) penetrating the septum 326 and discharging medication through chamber 328 and ports 329 formed in plate 306.

The plate 306 functions as part of a pump/valve subassembly 330 which includes a fluid transfer passageway for coupling reservoir volume 320 to outlet port 332. More particularly, plate 306 defines inlet port 336 opening via check valve 338 into pump chamber 340. Pump chamber 340 exits past outlet check valve 342 to safety valve 348. Safety valve 348 includes a valve element or diaphragm 350 having one face 352 exposed via port 354 to the pressure in reservoir volume 320. A second face 354 of diaphragm 350 is exposed via check valve 342 to the pressure produced in pump chamber 340.

When the reservoir pressure exceeds the pump chamber pressure, it forces diaphragm 350 in a direction to seal against valve seat 360 to thereby block unintended fluid flow from the reservoir to the outlet port 332. On the other hand, when it is intended to flow fluid from the reservoir to the outlet port, the pump chamber pressure is increased to unseat diaphragm 350. When diaphragm 350 is unseated, medication is able to flow through the passageway from the pump chamber 340 to the outlet port 332.

From the foregoing, it should now be apparent that an implantable ambient pressure medication delivery system has been described including means for preventing the unintended discharge of medication into the patient's body. The described means includes a safety mechanism depicted primarily in the embodiments of FIGS. 5-8 and 11 and a protective shell depicted primarily in FIGS. 9 and 10. Although distinctly discussed, it should be understood that these two techniques can be employed separately or in combination.

It should also be understood that although specific implementations have been described herein, it is recognized that variations and modifications will occur to those skilled in the art coming within the spirit and intended scope of the invention. Thus, for example only, it is pointed out that the check valves and safety valve illustrated could take many alternative forms using different valve elements and different mechanisms for producing the seating force, e.g., magnetic.

The invention claimed is:

1. An integrated medication delivery device configured to be implanted into a patient's body, said device comprising:
   a mounting structure;
   a movable wall carried by said mounting structure and defining a variable volume reservoir;
   a fill port for supplying medication to said reservoir;
   said mounting structure defining a fluid inlet port communicating with said reservoir, a fluid outlet port for discharging medication into said body, and a fluid path operable to transfer medication from said inlet port to said outlet port;
   said fluid path including a pump chamber, an inlet check valve that is biased to the closed state, that opens when pressure in the pump chamber is lower than reservoir pressure and located between said inlet port and said pump chamber, an outlet check valve that is biased to the closed state, that opens when pressure in the pump chamber is greater than reservoir pressure and located between said pump chamber and said outlet port, and a safety valve that is located between said outlet valve and said outlet port and is exposed to reservoir pressure by way of a channel that is not part of the fluid path;
   a pump actuator associated with said pump chamber operable to define a suction mode for pulling fluid via said inlet port from said reservoir into said pump chamber and a pressure mode that causes fluid from said pump chamber to be forced through the outlet check valve to said safety valve; and wherein
   said safety valve permits fluid flow when the pressure in said pump chamber exceeds the pressure in said reservoir and prevents fluid flow when the pressure in said reservoir exceeds the pressure in said pump chamber to prevent unintended medication discharge through said outlet port.

2. The device of claim 1 configured so that when implanted in a patient's body, both said movable wall and said outlet port are exposed to ambient pressure; and wherein said safety valve permits fluid flow during said pressure mode when said pump actuator acts to increase pressure in said pump chamber.

3. The device of claim 1 wherein said movable wall is comprised of a flexible non extensible non porous material.

4. The device of claim 1 wherein
said inlet check valve is biased to the closed state by a spring; and
said outlet check valve is biased to the closed state by a spring.

5. The device of claim 1 wherein said safety valve includes a valve element movable between open and closed positions and including means biasing said valve element to said closed position to normally prevent fluid flow to said outlet port; and
means for moving said safety valve element to said open position when said pump actuator increases pressure in said pump chamber.

6. The device of claim 5 including means responsive to an increase in pressure in said reservoir for increasing the sealing pressure on said safety valve element to prevent fluid flow to said outlet port.

7. The device of claim 1 wherein said mounting structure comprises a substantially planar structure.

8. The device of claim 1 wherein said fluid inlet port is located within said reservoir.

9. The device of claim 8 wherein
said mounting structure defines a safety valve port located within said reservoir and in spaced relation to said fluid inlet port; and
said safety valve port is in fluid communication with said safety valve by way of said channel.

10. The device of claim 9 wherein
said safety valve defines an open state that permits fluid flow and a closes state that prevents fluid flow; and
said safety valve is self-biased to the closed state.

11. The device of claim 9 wherein said mounting structure defines a first side and a second side opposite said first side, and said movable wall is carried by said first side of said mounting structure, said device further comprising
a cover secured to said second side of said mounting structure such that an internal compartment, in which said pump actuator is located, is defined therebetween.

12. The device of claim 9 wherein
said mounting structure includes first and second plates secured to one another;
said fluid inlet port and said safety valve port each extend though said first plate;
at least a portion of said outlet port is associated with said first plate; and
said pump actuator is associated with said second

* * * * *